United States Patent
Charyulu et al.

(10) Patent No.: US 11,629,120 B2
(45) Date of Patent: Apr. 18, 2023

(54) TRISODIUM SACUBITRIL VALSARTAN AND PROCESS FOR ITS PREPARATION

(71) Applicant: BIOCON LIMITED, Bangalore (IN)

(72) Inventors: Palle Venkata Raghavendra Charyulu, Madinaguda (IN); Pratik Rameshchandra Patel, Kalena (IN); Thirunelimada Devaiah Venu, Kudlu (IN); Reddy Avathu Vidyasagar, Kollipara (IN); Rajmahendra Shanmughasamy, Periyapanichery (IN)

(73) Assignee: BIOCON LIMITED, Electronic (IN)

( * ) Notice: Subject to any disclaimer, the term of this patent is extended or adjusted under 35 U.S.C. 154(b) by 0 days.

(21) Appl. No.: 17/090,033

(22) Filed: Nov. 5, 2020

(65) Prior Publication Data

US 2021/0122708 A1 Apr. 29, 2021

Related U.S. Application Data

(62) Division of application No. 16/345,576, filed as application No. PCT/IB2017/056706 on Oct. 28, 2017, now Pat. No. 10,995,060.

(30) Foreign Application Priority Data

Oct. 28, 2016 (IN) .............................. 201641037145
Nov. 11, 2016 (IN) .............................. 201641038689
Dec. 22, 2016 (IN) .............................. 201641043910

(51) Int. Cl.
C07C 233/47 (2006.01)
C07C 231/12 (2006.01)
C07D 257/04 (2006.01)

(52) U.S. Cl.
CPC .......... *C07C 233/47* (2013.01); *C07C 231/12* (2013.01); *C07D 257/04* (2013.01); *C07B 2200/13* (2013.01)

(58) Field of Classification Search
CPC ....... C07C 233/47; C07C 233/51; A61P 9/04; A61P 9/00; A61K 31/216
USPC ........................................................ 562/455
See application file for complete search history.

(56) References Cited

U.S. PATENT DOCUMENTS

| 5,217,996 | A | 6/1993 | Ksander |
| 8,877,938 | B2 | 11/2014 | Feng et al. |

FOREIGN PATENT DOCUMENTS

| CN | 105461647 B | 4/2016 |
| CN | 105503638 A | 4/2016 |
| CN | 105837464 A | 8/2016 |
| CN | 105693543 B | 8/2018 |
| EP | 2340828 A1 | 7/2011 |
| IN | 902CHE2015 | 2/2015 |
| WO | 200206253 A1 | 1/2002 |
| WO | 2007056546 A1 | 5/2007 |
| WO | 2016074651 A1 | 5/2016 |

OTHER PUBLICATIONS

Machine translation of CN 105837464, 2016.*
International Search Report and Written Opinion of WO 2018/078592 A1(PCT/IB2017/056706), with a publication date of May 3, 2018.
Dicarboxylic Acid Dipeptide Neutral Endopeptidase Inhibitors—Journal of Medicial Chemistry 1995 38 (10) pp. 1689-1700.

* cited by examiner

*Primary Examiner* — Ana Z Muresan
(74) *Attorney, Agent, or Firm* — Katten Muchin Rosenman LLP (57) ABSTRACT

The present invention provides for methyl)-4-amino-2R-methyl butanoic acid ethyl ester sodium salt, a novel process for the preparation of crystalline Form B of N-(3-carboxyl-1-oxopropyl)-(4S)-(p-phenylphenylmethyl)-4-amino-2R-methyl butanoic acid ethyl ester sodium salt.

2 Claims, 7 Drawing Sheets

TRISODIUM SACUBITRIL VALSARTAN AND PROCESS FOR ITS PREPARATION

CROSS REFERENCE TO RELATED APPLICATIONS

This application is a divisional application of U.S. patent application Ser. No. 16/345,576, filed on Apr. 26, 2019, which is a 35 U.S.C. § 371 national stage application of International Application No. PCT/IB2017/056706, filed on Oct. 28, 2017, which claims the benefit of Indian Patent Application 201641043910, filed on Dec. 22, 2016, Indian Patent Application 201641038689, filed on Nov. 11, 2016, and Indian Patent Application 201641037145 filed Oct. 28, 2016, where the disclosures of each are incorporated herein by reference in their entirety for all purposes.

TECHNICAL FIELD

The present invention relates to methods for preparation of amorphous form of Sacubitril Valsartan Trisodium complex represented by the structural Formula-I and processes for the preparation thereof.

FORMULA - 1

The present invention also relates to novel crystalline forms of N-(3-carboxyl-1-oxopropyl)-(4S)-(p-phenylphenylmethyl)-4-amino-2R-methyl butanoic acid ethyl ester sodium salt [Sacubitril sodium] represented by the structural Formula-II and processes for the preparation thereof.

FORMULA II

The present invention also relates to novel crystalline forms of (S)—N-(5 1-Carboxy-2-Methyl-Prop-1-yl)-N-Pentanoyl-N-[2'-(1H-Tetrazol-5-yl)-Biphenyl-4-yl-Methyl]-Amine disodium salt [Valsartan disodium] represented by the structural Formula-I and processes for the preparation thereof.

FORMULA III

BACKGROUND AND PRIOR ART OF THE DISCLOSURE

ENTRESTO is a combination of sacubitril, a neprilysin inhibitor, and valsartan, an angiotensin II receptor blocker, indicated to reduce the risk of cardiovascular death and 10 hospitalization for heart failure in patients with chronic heart failure (NY HA Class II-IV) and reduced ejection fraction.

Sacubitril sodium is disclosed in U.S. Pat. No. 5,217,996 A along with methods for preparation of Sacubitril sodium.

Journal of Medicinal Chemistry, 1995, 38 (10), pp 1689-1700 discloses the process for preparation of Sacubitril sodium.

CN105503638A discloses process of preparation of Sacubitril sodium using ethanol and tetrahydrofuran (1:1) mixed solvent.

CN105693543 discloses various salts of Sacubitril like Sacubitril potassium, magnesium Sacubitril, Sacubitril t-butyl amine salt, Sacubitril ethanolamine salt, Sacubitril piperazine, Sacubitril calcium salt, Sacubitril tromethamine salt, Sacubitril triethanolamine salt. This patent application also discloses Sacubitril magnesium amorphous of X-ray powder diffraction pattern.

CN105837464 A discloses various crystalline forms of Sacubitril sodium such as Form A, Form B, Form C and Form D along with amorphous form.

This Chinese patent application discloses Sacubitril sodium of crystalline Form A which is characterized by X-ray powder diffraction pattern (using Cu—K radiation) the characteristic diffraction peaks corresponding 2θ values are 6.0 ± 0.2°, 6.6 ± 0.2°, 9.0 ± 0.2°, 12.2 ± 0.2°, 13.2 ± 0.2°, 15.1 ± 0.2°, 17.1 ± 0.2°, 17.8 ± 0.2°, 18.3 ± 0.2°, 19.2 ± 0.2°, 19.7 ± 0.2°, 20.2 ± 0.2°, 20.8 ± 0.2°, 21.4 ± 0.2°, 21.6 ± 0.2°, 22.6 ± 0.2°, 26.7 ± 0.2°.

This Chinese patent application discloses Sacubitril sodium of crystalline Form B which is characterized by X-ray powder diffraction pattern (using Cu—K radiation) the characteristic diffraction peaks corresponding 2θ values are 6.1 ± 0.2°, 7.1 ± 0.2°, 7.7 ± 0.2°, 11.8 ± 0.2°, 12.3 ± 0.2°, 12.6 ± 0.2°, 13.6 ± 0.2°, 15.4 ± 0.2°, 16.4 ± 0.2°, 19.9 ± 0.2°, 20.1 ± 0.2°, 23.7 ± 0.2°, 24.0 ± 0.2°, 24.8 ± 0.2°, 25.9 ± 0.2°, 26.2 ± 0.2°.

This Chinese patent application discloses Sacubitril sodium of crystal line Form C which is characterized by X-ray powder diffraction pattern (using Cu—K radiation) the characteristic diffraction peaks corresponding 2θ values are 6.3 ± 0.2°, 7.3 ± 0.2°, 12.7 ± 0.2°, 14.7 ± 0.2°, 15.9 ± 0.2°, 18.5 ± 0.2°, 19.2 ± 0.2°, 22.4 ± 0.2°, 22.7 ± 0.2°, 23.6 ± 0.2°, 27.0 ± 0.2°.

This Chinese patent application discloses Sacubitril sodium of crystalline Form D which is characterized by X-ray powder diffraction pattern (using Cu—K radiation) the characteristic diffraction peaks corresponding 2θ values are value 6.3 ± 0.2°, 7.3 ± 0.2°, 12.0 ± 0.2°, 12.8 ± 0.2°, 16.6 ± 0.2°, 17.0 ± 0.2°, 18.5 ± 0.2°, 20.0 ± 0.2°, 21.7 ± 0.2°, 22.5 ± 0.2°, 23.9 ± 0.2°, 26.3 ± 0.2°, 27.1 ± 0.2°.

PCT Publication No. WO2016074651A1 discloses various crystalline Sacubitril amine salts. This PCT publication discloses the crystalline salt of Sacubitril with cyclohexyl amine, the characteristic diffraction peaks corresponding 2θ values are 7.4, 15.0, 18.0, 19.9, 21.6 (° ± 0.2° 2θ:), the crystalline salt of Sacubitril with isopropyl amine, the characteristic diffraction peaks corresponding 2θ values are 3.1, 9.5, 12.6, 18.5, 24.6 (° ± 0.2° 2θ:), the crystalline salt of Sacubitril with isopropyl amine, the characteristic diffraction peaks corresponding 2θ values are 8.0, 9.8, 16.1, 17.8, 20.2 (° ± 0.2° 2θ:).

PCT Publication No. WO2016074651A1 discloses various crystalline and semi crystalline forms of Sacubitril calcium salt. This PCT discloses the crystalline form I of crystalline Sacubitril calcium salt with characteristic diffraction peaks corresponding 2θ values are 3.6, 6.4, 8.4, 10.8, 14.5, 17.7, 20.6 and 22.5 (° ± 0.2° 2θ:). This PCT discloses the crystalline form II of crystalline Sacubitril calcium salt with characteristic diffraction peaks corresponding 2θ values are 3.2, 7.4, 11.4, 12.9, 16.2, 18.7, 22.5, 23.7 and 27.1(° ± 0.2° 2θ:).

This PCT discloses the semicrystalline form III of the calcium salt of Sacubitril with characteristic diffraction peaks corresponding 2θ values are 4.0 and 4.7 ± 0.2°. This PCT discloses the semi crystal line form IV of the calcium salt of Sacubitril with characteristic diffraction peaks corresponding 2θ values are 4.6; 6.4 and 14.3 ± 0.2°. This PCT publication also discloses the comparative stability study of crystalline Sacubitril calcium salt and crystalline Sacubitril sodium salt. This study shows a sample of the calcium salt of Sacubitril (form I) upon exposing to the temperature of 80°C at 0% relative humidity (RH) fit and 75% RH for 3 days. The crystalline state of the calcium salt of Sacubitril did not change during this time period. The same experiment was also conducted with the sodium salt of Sacubitril, which exhibited a high rate of polymorph instability and at 75% RH the sample became completely amorphous (see Table 1).

TABLE 1

Stability of solid forms of sacubitril salts

| sample | X-ray powder analysis | Result after loading of the sample at 80° C./0% RH | Result after loading of the sample at 80° C./75% RH |
| --- | --- | --- | --- |
| calcium salt of sacubitril | Crystalline sample (form I) | Crystalline sample (form I)I | Crystalline sample (form I)I |
| sodium salt of sacubitril | Semicrystalline phase | Semicrystalline phase | Amorphous sample |

Thus there is a need to develop stable crystalline polymorphs of Sacubitril sodium, with the process involving be simple and cost-effective.

PCT Publication No. WO 2007056546 A1 discloses crystalline Valsartan disodium salt, but does not disclose any analytical data or process for preparation of the same;

PCT Publication No. WO 200206253 A1 discloses amorphous and crystal line Valsartan disodium salt; Example 5 of the publication discloses a process for the preparation of the Valsartan disodium salt involving dissolving the valsartan in ethanol, mixing with 2 N sodium hydroxide solution and concentrating by evaporation, and the residue is evaporated with each of ethanol and ethyl acetate. The white residue is stirred in hot acetonitrile and filtered by suction at room temperature. Drying in a high vacuum at 80°C, overnight yields (S)—N-(1-carboxy-2-methyl-prop-1-yl)-N-pentanoyl-N-[2'(1Htetrazol-5-yl)-biphenyl-4-ylmethyl]-amine disodium salt as a white powder. Melting point from 260°C, brownish discolouration at 295°C. There is no reference provided for the nature of the product whether it is amorphous or crystalline.

Example 11 of the same PCT publication No. WO 200206253 discloses a process for the preparation of the Hydrate of valsartan disodium salt (2.4 ± 1.0 mole H2O). A solution was valsartan in isopropanol was added 2N sodium hydroxide solution dropwise at ca. 25°C. The clear solution (pH 7.2) was concentrated under vacuum at ca.40°C. The amorphous residue of the disodium salt was suspended in 100 ml of isopropanol, and water was removed by concentrating under vacuum once more at ca. 40°C and degassing. The amorphous residue was suspended in 75 ml of acetone and 2 ml of water at ca. 40°C. At ca. 25-30°C, 200 ml of tert.-butylmethylether were added, whereby constituents that were initially smeary were gradually transformed into a crystalline suspension. After stirring over night at ca. 25°C, the suspension was cooled to 10°C and after ca. 1 hour was filtered by suction whilst excluding atmospheric moisture. Washed with 20 ml of tert.-butylmethylether. The moist filter cake was dried over night at ca. 30 mbar and at 30°C. A colourless, slightly hygroscopic crystal powder was obtained. There is no XRD diffractogram provided but 2::values with intensity are provided as below.

| 2θ | Intensity |
|------|----------|
| 4.7  | strong   |
| 9.1  | strong   |
| 13.3 | weak     |
| 13.7 | weak     |
| 15.6 | medium   |
| 16.4 | medium   |
| 17.2 | medium   |
| 17.9 | medium   |
| 18.7 | medium   |
| 19.6 | medium   |
| 21.3 | medium   |
| 21.9 | medium   |
| 22.8 | strong   |
| 24.0 | weak     |
| 24.8 | weak     |
| 25.5 | weak     |
| 26.5 | medium   |
| 26.8 | weak     |
| 27.3 | weak     |
| 27.8 | weak     |
| 28.6 | weak     |
| 29.4 | weak     |
| 29.9 | medium   |

The above process as described is laborious and also not cost effective. Also as disclosed in the example 11 the crystalline valsartan disodium hydrate is hygroscopic and hence might not be stable and shelf life would get affected. Thus there is a need to develop stable crystalline polymorphs of valsartan disodium, with the process involving be simple and cost-effective.

U.S. Pat. No. 8,877,938 B2 discloses Trisodium [3-((1S, 3R)-1-biphenyl-4-ylmethyl-3-ethoxycarbonyl-1-butylcarbamoyl)propionate-(S)-3-m methyl-2-m pentanoyl{2↓-(tetrazol-5-ylate)biphenyl-4-y 1 methyl}amino)butyrate] hemipentahydrate in crystalline form.

EP Patent application no. 2340828 discloses the Trisodium [3-((1S, 3R)-1-biphenyl-4-ylmethyl-3-ethoxycarbonyl-1-butylcarbamoyl)propionate-(S)-3-m methyl-2→(pentanoyl{2↓-(tetrazol-5-ylate)biphenyl-4-y ylmethyl}amino)butyrate] in amorphous form.

CN 105461647 application discloses sodium [3-((1S, 3R)-1-biphenyl-4-ylmethyl-3-ethoxycarbonyl-1-butylcarbamoyl)propionate-(S)-3-m methyl-2-m pentanoyl{2↓-(tetrazol-5-ylate)biphenyl-4--y lmethyl}amino)butyrate]in, ∮ and .:amorphous form.

PCT Publication No. WO 2007056546 A1 discloses amorphous sacubitril valsartan trisodium and various processes for preparation thereof.

The above process as described is laborious and also not cost effective. Thus there is a need to develop stable amorphous form of sacubitril valsartan trisodium, with the process involving be simple and cost-effective.

SUMMARY OF THE INVENTION

One aspect of the present invention is to provide a crystalline Form B1 of N-(3-carboxyl-1-oxopropyl)-(4S)-(p-phenylphenylmethyl)-4-amino-2R-methyl butanoic acid ethyl ester sodium salt and a process for the preparation thereof.

Second aspect of the present invention is to provide a process for preparation of crystalline Form B1 of N-(3-carboxyl-1-oxopropyl)-(4S)-(p-phenylphenylmethyl)-4-amino-2R-methyl butanoic acid ethyl ester sodium salt by dissolving N-(3-carboxyl-1-oxopropyl)-(4S)-(p-phenylphenylmethyl)-4-amino-2R-methyl butanoic acid ethyl ester sodium salt in a suitable solvent, stirring at elevated temperature for a suitable time followed by cooling to an ambient temperature followed by isolation of crystalline Form B1 of N-(3-carboxyl-1-oxopropyl)-(4S)-(p-phenylphenylmethyl)-4-amino-2R-methyl butanoic acid ethyl ester sodium salt.

Third aspect of the present invention is to provide a crystalline Form B2 of N-(3-carboxyl-1-oxopropyl)-(4S)-(p-phenylphenylmethyl)-4-amino-2R-methyl butanoic acid ethyl ester sodium salt and a process for the preparation thereof.

Fourth aspect of the present invention relates to a process for preparation of crystalline Form B2 of N-(3-carboxyl-1-oxopropyl)-(4S)-(p-phenylphenylmethyl)-4-amino-2R-methyl butanoic acid ethyl ester sodium salt by acidifying N-(3-carboxyl-1-oxopropyl)-(4S)-(p-phenylphenylmethyl)-4-amino-2R-methyl butanoic acid ethyl ester calcium salt into free acid using aq. HCl in a suitable solvent Reacting the N-(3-carboxyl-1-oxopropyl)-(4S)-(p-phenylphenylmethyl)-4-amino-2R-methyl butanoic acid ethyl ester with a suitable base in a suitable solvent stirring at ambient temperature for a suitable time followed by cooling to an ambient temperature followed by isolation of crystal line Form B2 of N-(3-carboxyl-1-oxopropyl)-(4S)-(p-phenylphenylmethyl)-4-amino-2R-methyl butanoic acid ethyl ester sodium salt.

Fifth aspect of the present invention is to provide processes for the preparation of crystal line Form B of N-(3-carboxyl-1-oxopropyl)-(4S)-(p-phenylphenylmethyl)-4-amino-2R-methyl butanoic acid ethyl ester sodium salt.

Sixth aspect of the present invention relates to a process for preparation of crystal line Form B of N-(3-carboxyl-1-oxopropyl)-(4S)-(p-phenylphenylmethyl)-4-amino-2R-methyl butanoic acid ethyl ester sodium salt by acidifying N-(3-carboxyl-1-oxopropyl)-(4S)-(p-phenylphenylmethyl)-4-amino-2R-methyl butanoic acid ethyl ester calcium salt into free acid using aq. HCl in a suitable solvent Reacting the N-(3-carboxyl-1-oxopropyl)-(4S)-(p-phenylphenylmethyl)-4-amino-2R-methyl butanoic acid ethyl ester with a suitable base in a suitable solvent, stirring at ambient temperature for a suitable time followed by cooling to an ambient temperature followed by isolation of crystalline Form B of N-(3-carboxyl-1-oxopropyl)-(4S)-(p-phenylphenylmethyl)-4-amino-2R-methyl butanoic acid ethyl ester sodium salt.

Seventh aspect of the present invention is to provide a crystalline Form B of (S)—N-(1-Carboxy-2-Methyl-Prop-1-yl)-N-Pentanoyl-N-[2'-(1H-Tetrazol-5-yl)-Biphenyl-4-yl-Methyl]-Amine disodium salt.

Eighth aspect of the present invention is to provide a crystalline Form B of (S)—N-(1-Carboxy-2-Methyl-Prop-1-yl)-N-Pentanoyl-N-[2'-(1H-Tetrazol-5-yl)-Biphenyl-4-yl-Methyl]-Amine disodium salt from amorphous (S)—N-(1-Carboxy-2-Methyl-Prop-1-yl)-N-Pentanoyl-N-[2'-(1H-Tetrazol-5-yl)-Biphenyl-4-yl-Methyl]-Amine disodium salt.

Ninth aspect of the present invention is to provide a crystalline Form B of (S)—N-(1-Carboxy-2-Methyl-Prop-1-yl)-N-Pentanoyl-N-[2'-(1H-Tetrazol-5-yl)-Biphenyl-4-yl-Methyl]-Amine disodium salt by dissolving amorphous (S)—N-(1-Carboxy-2-Methyl-Prop-1-yl)-N-Pentanoyl-N-[2'-(1H-Tetrazol-5-yl)-Biphenyl-4-yl-Methyl]-Amine in a suitable solvent in presence of a suitable sodium source, stirring at an elevated temperature, removal of the solvent azeotropically followed by isolation of crystalline Form B of N-(3-carboxyl-1-oxopropyl)-(4S)-(p-phenylphenylmethyl)-4-amino-2R-methyl butanoic acid ethyl ester sodium salt.

Tenth aspect of the present invention is to provide crystal line Form P of (S)—N-(1-Carboxy-2-Methyl-Prop-1-yl)-N-Pentanoyl-N-[2'-(1H-Tetrazol-5-yl)-Biphenyl-4-yl-Methyl]-Amine disodium salt from amorphous (S)—N-(1-Carboxy-2-Methyl-Prop-1-yl)-N-Pentanoyl-N-[2'-(1H-Tetrazol-5-yl)-Biphenyl-4-yl-Methyl]-Amine using an aromatic hydrocarbon as the solvent.

Eleventh aspect of the present invention is to provide crystalline Form B of (S)—N-(1-Carboxy-2-Methyl-Prop-1-yl)-N-Pentanoyl-N-[2'-(1H-Tetrazol-5-yl)-Biphenyl-4-yl-Methyl]-Amine disodium salt from amorphous (S)—N-(1-Carboxy-2-Methyl-Prop-1-yl)-N-Pentanoyl-N-[2'-(1H-Tetrazol-5-yl)-Biphenyl-4-yl-Methyl]-Amine using a sodium source and a suitable solvent.

Twelfth aspect of the present invention relates to process for preparation of amorphous form of sacubitril valsartan trisodium by dissolving sacubitril valsartan trisodium in a suitable solvent.

Thirteenth aspect of the present invention relates to process for preparation of amorphous form of sacubitril valsartan trisodium by acidifying calcium salt of sacubitril to sacubitril free acid and treating with sodium hydroxide and valsartan in presence of a suitable solvent.

Fourteenth aspect of the present invention relates to process for preparation of amorphous solid dispersion of sacubitril valsartan trisodium with an excipient by acidifying calcium salt of sacubitril to sacubitril free acid and treating with sodium hydroxide, excipient and valsartan in presence of a suitable solvent.

The term "suitable solvent" used in the present invention is selected from, but not limited to 'aliphatic hydrocarbon solvents" such as heptane, hexane, pentane, acetone, methyl ethyl ketone, methyl isobutyl ketone, ethyl acetate, methyl acetate, isopropyl acetate, n-butyl acetate, methanol, ethanol, n-propanol, isopropanol, n-butanol, isobutanol, tert-butanol and the like." poly hydroxy alkanes" such as ethylene glycol, propane 1,2 diol, propane 1,3 diol, butane 1,2 diol, butane 2,3 diol, aromatic hydrocarbon solvents such as toluene, benzene and the like.

The term 'sodium source_ used in the present invention is selected from, but not limited to sodium hydroxide, sodium carbonate, sodium bicarbonate, sodium methoxide, sodium ethoxide and the like.

The term 'excipient_ used in the present invention is selected from, but not limited to microcrystalline cellulose, hydroxypropyl methyl cellulose, silicon dioxide, hydroxypropyl cellulose, cellulose acetate, mannitol, sorbitol and the like.

BRIEF DESCRIPTION OF THE FIGURES

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure wherein.

The method of analysis of the compounds represented in the figures as above are as below:

PXRD Analysis

A bout 300 mg of powder sample was taken onto the sample holder and was tightly packed on the sample holder uniformly by means of glass slide and Powder X-ray diffraction was recorded on Bruker D8 Advance diffractometer (Bruker-AX 5, Karlsruhe, Germany) using Cu—K X-radiation ($\approx$=1.5406 i) at 40 kV and 30 mA powder. X-ray diffraction patterns were collected over the 2::range 3⁻50é at a scan rate of 1é/min.

DSC Analysis

DSC was performed on a Mettler Toledo DSC 822e module. 4-6 mg of sample was placed in crimped but vented aluminium sample pans. The temperature range was from 30-250 éC @ 10 éC/min. Samples were purged by a stream of nitrogen flowing at 80 mL/min.

IR Analysis

IR was performed on a Fisher Scientific (NICOL ET-iS50-FTIR). A bout 5 mg of sample was spread over the region of diamond AT R sampling station and collected the sample spectrum between 4000 cm-1 to 400 cm-1 to obtain a spectrum of suitable intensity (above 60% transmission at 2000 cm-1).

DETAILED DESCRIPTION OF THE INVENTION

The term "suitable solvent" used in the present invention is selected from, but not limited to "ester solvents" such as ethyl acetate, methyl acetate, isopropyl acetate, n-butyl acetate and the like; "ether solvents" such as tetrahydrofuran, di methyl ether, diethyl ether, diisopropyl ether, methyl tert-butyl ether (MTBE), 1,4-dioxane and the like; "hydrocarbon solvents" such as toluene, hexane, heptane, pet ether, xylene, cyclohexane and the like; "polar aprotic solvents" such as di methyl acetamide, dimethylsulfoxide, dimethylformamide, N-methyl-2-pyrrolidone and the like; "ketone solvents" such as acetone, methyl ethyl ketone, methylisobutyl ketone and the like; "alcoholic solvents" such as methanol, ethanol, n-propanol, isopropanol, n-butanol, isobutanol, tert-butanol and the like; "chlorinated solvents" such as dichloromethane, chloroform, dichloroethane, carbon tetrachloride and the like; "nitrile solvents" such as acetonitrile, butyronitrile, isobutyronitrile and the like;

"polar solvent" such as water or mixtures thereof; 'aliphatic hydrocarbon solvents" such as heptane, hexane, pentane and the like; "aliphatic hydrocarbon solvents" such as acetone, methyl ethyl ketone, methylisobutyl ketone, ethyl acetate, methyl acetate, isopropyl acetate, n-butyl acetate, methanol, ethanol, n-propanol, isopropanol, n-butanol, isobutanol, tert-butanol and the like." poly hydroxy alkanes" such as ethylene glycol, propane 1,2 diol, propane 1,3 diol, butane 1,2 diol, butane 2,3 diol, aromatic hydrocarbon solvents such as toluene, benzene and the like.

The term 'sodium source_ used in the present invention is selected from, but not limited to sodium hydroxide, sodium carbonate, sodium bicarbonate, sodium methoxide, sodium ethoxide and the like.

The embodiments of the present invention are further described using specific examples herein after. The examples are provided for better understanding of certain embodiments of the invention and not, in any manner, to limit the scope thereof. Possible modifications and equivalents apparent to those skilled in the art using the teachings of the present description and the general art in the field of the invention shall also form the part of this specification and are intended to be included within the scope of it.

Example 1: Preparation of Crystalline Form B1 of N-(3-carboxyl-1-oxopropyl)-(4S)-(p-phenylphenyl-methyl)-4-amino-2R-methyl Butanoic Acid Ethyl Ester Sodium Salt Amorphous Sacubitril sodium (1 g) in methyl isobutyl ketone (5 mL) was stirred for 10 min at 25-30 éC. The temperature of reaction mass was raised to 40-45 éC to get the clear solution. Stirred the reaction mass for 1 hr at 40-45° C. During stirring, clear solution gradually transformed to crystalline suspension. The suspension was then cooled to 25-30éC. The suspension was stirred at same temperature for 60 min. The sol id was collected by filtration and dried for 12 hrs at 30-35éC under vacuum to yield N-(3-carboxyl-1-oxopropyl)-(4S)-(p-phenylphenylmethyl)-4-amino-2R-methyl butanoic acid ethyl ester sodium salt as crystal line Form B1.

Figure 1:
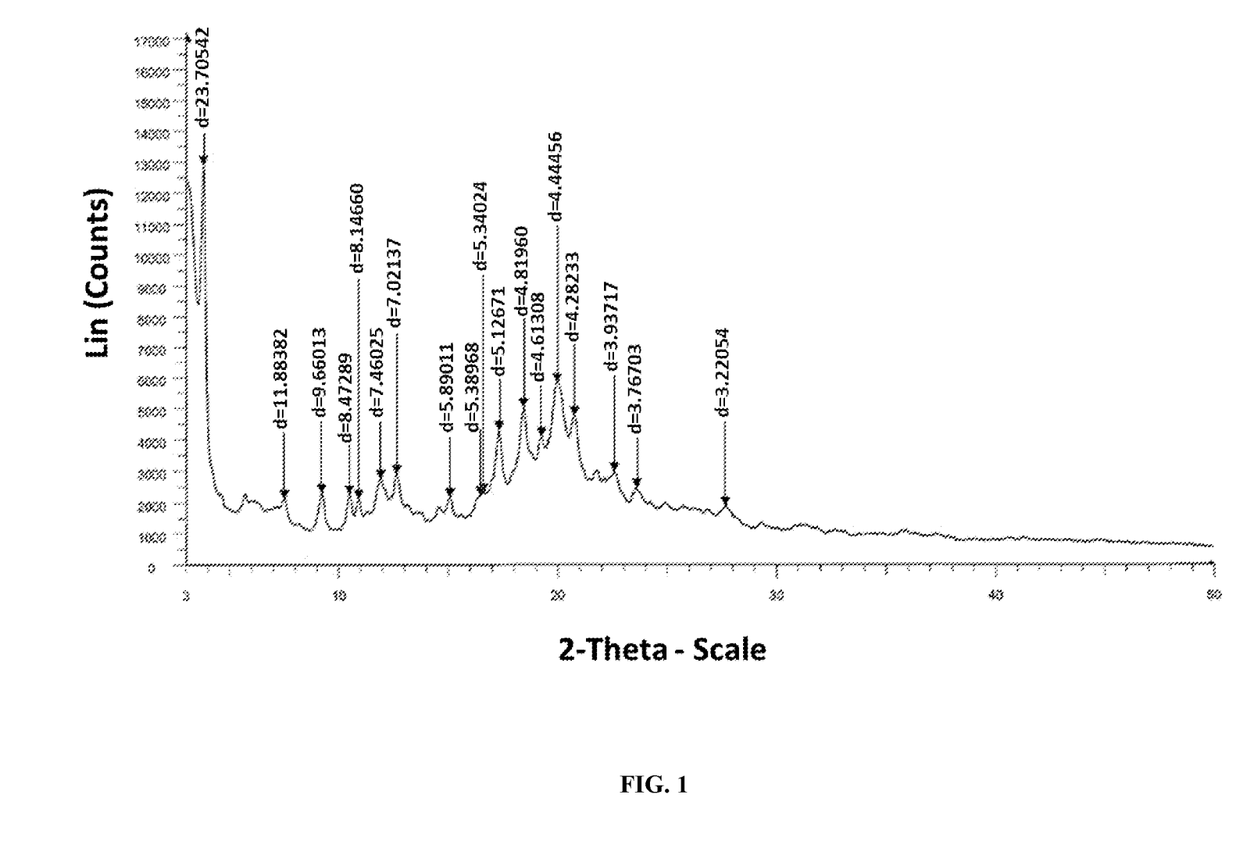
FIG. 1 Illustrates the PXRD pattern of crystal line Form B1 of N-(3-carboxyl-1-oxopropyl)-(4S)-(p-phenylphenylmethyl)-4-amino-2R-methyl butanoic acid ethyl ester sodium salt.

The PXRD pattern of Form B1 of N-(3-carboxyl-1-oxopropyl)-(4S)-(p-phenylphenylmethyl)-4-amino-2R-methyl butanoic acid ethyl ester sodium salt is shown in FIG. 1.

IR (cm$^{-1}$): 514.62, 603.40, 651.26, 695.70, 733.58, 760.93, 819.75, 850.60, 936.35, 1008.03, 1025.23, 1085.23, 1159.20, 1190.94, 1265.08, 1409.04, 1487.36, 1562.78, 1646.99, 1721.91, 2936.16, 2977.43, 3336.91.

Example 2: Preparation of Crystalline Form B2 of N-(3-carboxyl-1-oxopropyl)-(4S)-(p-phenylphenyl-methyl)-4-amino-2R-methyl Butanoic Acid Ethyl Ester Sodium Salt Sacubitril calcium (25 g.) in ethyl acetate was added 5 N HCl to adjust the pH to 1 to 1.5 and stirred for 10 to 20 minutes. The reaction mass was diluted with water and layers were separated. The aqueous layer was extracted with ethyl acetate, organic layers were combined and concentrated to yield Sacubitril free acid. The concentrated mass of Sacubitril free acid, was added ME K (Methyl ethyl ketone) (3.0 vol.) and 0.5N NaOH (0.9 eq). The reaction mass was stirred for 2 hrs at 25° C. The reaction mass was concentrated and given acetonitrile strip off. MDC (3.0 vol.) and Toluene (6.0 vol.) were added to the residue and partially concentrated at 50° C. to 5.0 vol. stage and then added n-Heptane (5.0 vol.). Stirred the obtained solid for 1 hour. Filtered and washed the solid with n-heptane. Dried the Sacubitril sodium under vacuum at 50° C.

Figure 2:
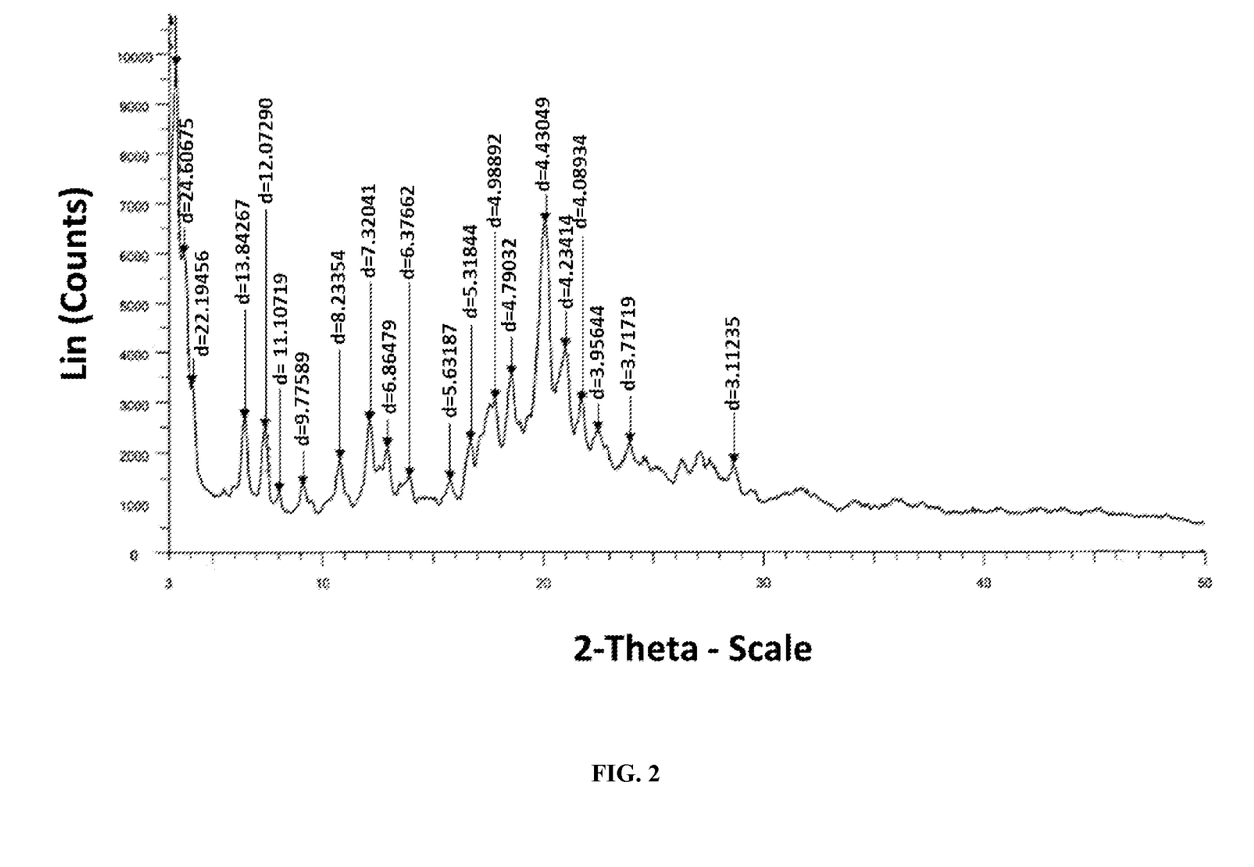
FIG. 2: Illustrates the PXRD pattern of crystalline Form B2 of N-(3-carboxyl-1-oxopropyl)-(4S)-(p-phenylphenylmethyl)-4-amino-2R-methyl butanoic acid ethyl ester sodium salt.

The PXRD pattern of Form B2 of N-(3-carboxyl-1-oxopropyl)-(4S)-(p-phenylphenylmethyl)-4-amino-2R-methyl butanoic acid ethyl ester sodium salt is shown in FIG. 2.

IR (cm$^{-1}$): 497.75, 552.98, 608.37, 651.29, 692.67, 732.22, 760.91, 812.97, 839.37, 872.29, 909.96, 933.29, 1015.49, 1099.64, 1128.13, 1162.15, 1189.91, 1242.81, 1270.88, 1296.59, 1372.08, 1416.31, 1434.94, 1487.75, 1523.64, 1564.18, 1647.96, 1708.70, 1731.66, 2916.44, 2978.88, 3030.21, 3351.01.

Example 3: Preparation of Crystalline Form B of N-(3-carboxyl-1-oxopropyl)-(4S)-(p-phenylphenyl-methyl)-4-amino-2R-methyl Butanoic Acid Ethyl Ester Sodium Salt Sacubitril sodium amorphous (1 g) was added to n-heptane (50 mL) and stirred for 10 min at 25-30 éC. The reaction mass temperature was slowly raised to 90-95 éC and water was removed azeotropically. During azeotropic distillation, cl ear solution gradually transformed to crystalline suspension. The suspension was cooled to 25-30° C. The suspension was stirred at same temperature for 15-30 min. The solid was collected by filtration and dried for 12 hrs at 30-35éC under vacuum to yield N-(3-carboxyl-1-oxopropyl)-(4S)-(p-phenylphenylmethyl)-4-amino-2R-methyl butanoic acid ethyl ester sodium salt as crystal line Form B.

Example 4: Preparation of Crystalline Form B of N-(3-carboxyl-1-oxopropyl)-(4S)-(p-phenylphenyl-methyl)-4-amino-2R-methyl Butanoic Acid Ethyl Ester Sodium Salt Sacubitril calcium (1.0 Kg.) in ethyl acetate (7.0 Vol) was added 5 N HCl to adjust to pH 1 to 1.5 and stirred for 10 to 20 minutes. The reaction mass was diluted with water and aqueous layers were separated. The aqueous layer was extracted with ethyl acetate, organic layer were combined and concentrated to yield sacubitril free acid. The concentrated mass of sacubitril free acid, was added n-heptane (10.0 V) and aq NaOH (0.9 eq.) and stirred for 10 min at 25-30 éC. The reaction mass temperature was slowly raised to 90-95 éC and water was removed azeotropically. The clear solution gradually transformed to crystalline suspension. The suspension was cooled to 25-30 éC. The suspension was stirred at same temperature for 15-30 min. The solid was collected by filtration and dried for 12 hrs at 30-35 éC under vacuum to yield 0.8 Kg of N-(3-carboxyl-1-oxopropyl)-(4S)-(p-phenyl phenylmethyl)-4-amino-2R-methyl butanoic acid ethyl ester sodium salt as crystalline form B.

Figure 3:
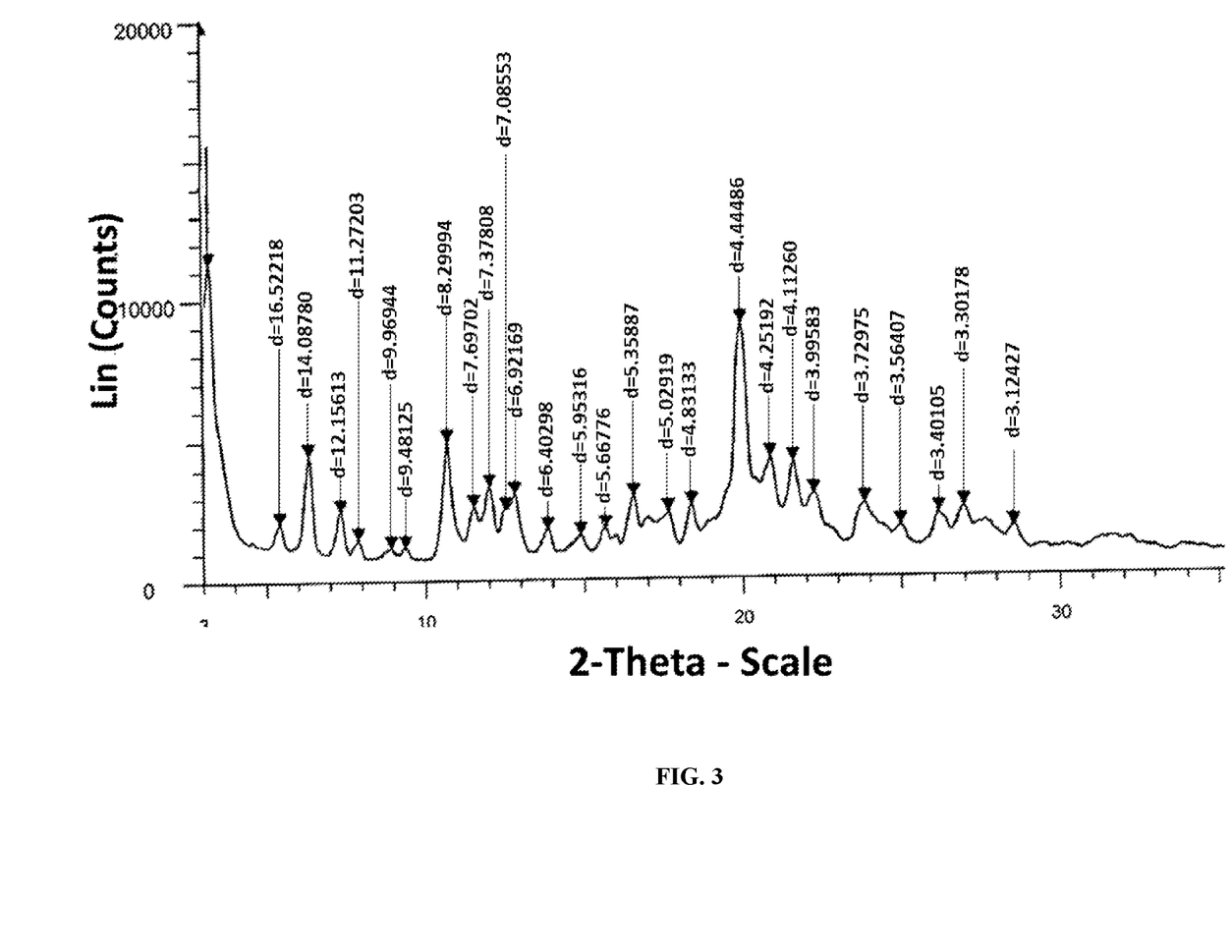
FIG. 3: Illustrates the PXRD pattern of crystalline Form B of N-(3-carboxyl-1-oxopropyl)-(4S)-(p-phenylphenylmethyl)-4-amino-2R-methyl butanoic acid ethyl ester sodium salt.

The PXRD pattern of crystalline Form B of N-(3-carboxyl-1-oxopropyl)-(4S)-(p-phenylphenylmethyl)-4-amino-2R-methyl butanoic acid ethyl ester sodium salt is shown in FIG. 3.

Example 5: Preparation of Crystalline Form B of (S)—N-(1-Carboxy-2-Methyl-Prop-1-yl)-N-Pentanoyl-N-[2'-(1H-Tetrazol-5-yl)-Biphenyl-4-yl-Methyl]-Amine Disodium Salt (S)—N-(1-Carboxy-2-Methyl-Prop-1-yl)-N-Pentanoyl-N-[2'-(1H-Tetrazol-5-yl)-Biphenyl-4-yl-Methyl]-Amine disodium salt (3.0 g) was taken in to a RBF and MIBK (Methyl iso butyl ketone) (150 ml) was added. The temperature of reaction mass was slowly raised to reflux and water was removed azeotropically. During azeotropic distillation, the clear solution gradually transformed to crystalline suspension. The suspension thus formed was cooled to 85-90° C. The suspension mass was stirred at same temperature for 15-30 min. Filtered the reaction mass. The wet cake was dried for 10-12 hr at 30-35° C. under vacuum to yield crystalline Form B of (S)—N-(1-Carboxy-2-Methyl-Prop-1-yl)-N-Pentanoyl-N-[2'-(1H-Tetrazol-5-yl)-Biphenyl-4-yl-Methyl]-Amine disodium salt (2.5 g).

Example 6: Preparation of Crystalline Form B of (S)—N-(1-Carboxy-2-Methyl-Prop-1-yl)-N-Pentanoyl-N-[2'-(1H-Tetrazol-5-yl)-Biphenyl-4-yl-Methyl]-Amine Disodium Salt To a solution of amorphous (S)—N-(1-Carboxy-2-Methyl-Prop-1-yl)-N-Pentanoyl-N-[2'-(1H-Tetrazol-5-yl)-Biphenyl-4-yl-Methyl]-Amine (5.0 g) in 250 ml MIBK (Methyl iso butyl ketone) was added 50% aq. sodium hydroxide (0.96 g.) solution. The temperature of reaction mass was raised to reflux and water was removed azeotropically. During azeotropic distillation, clear solution gradually transformed to crystal line suspension. The suspension was cooled to 85-90° C. The suspension mass was stirred at same temperature for 15-30 min. Filtered the reaction mass. The wet cake was dried for 10-12 hr at 30-35° C. under vacuum to yield crystalline Form B of (S)—N-(1-Carboxy-2-Methyl-Prop-1-yl)-N-Pentanoyl-N-[2'-(1H-Tetrazol-5-yl)-Biphenyl-4-yl-Methyl]-Amine disodium salt (4.48 g).

Example 7: Preparation of Crystalline Form B of (S)—N-(1-Carboxy-2-Methyl-Prop-1-yl)-N-Pentanoyl-N-[2'-(1H-Tetrazol-5-yl)-Biphenyl-4-yl-Methyl]-Amine Disodium Salt To a solution of amorphous (S)—N-(1-Carboxy-2-Methyl-Prop-1-yl)-N-Pentanoyl-N-[Z-(1H-Tetrazol-5-yl)-Biphenyl-4-yl-Methyl]-Amine (1.0 Kg) in MIBK (10 Vol.) (Methyl iso butyl ketone) was added 30% Sodium Methoxide solution in methanol solution (0.88 Kg). The temperature of reaction mass was raised to reflux and methanol was removed azeotropically. The suspension was maintain under reflux for around 2 hr. The suspension was cooled to around 25 to 30° C. The suspension mass was stirred at same temperature for 15-30 min. Filtered the reaction mass. The wet cake was dried for 10-12 hr at 65 to 80° C. under vacuum to yield 0.88 Kg of crystalline Form B of (S)—N-(1-Carboxy-2-Methyl-Prop-1-yl)-N-Pentanoyl-N-[2'-(1H-Tetrazol-5-yl)-Biphenyl-4-yl-Methyl]-Amine disodium salt.

Figure 4:
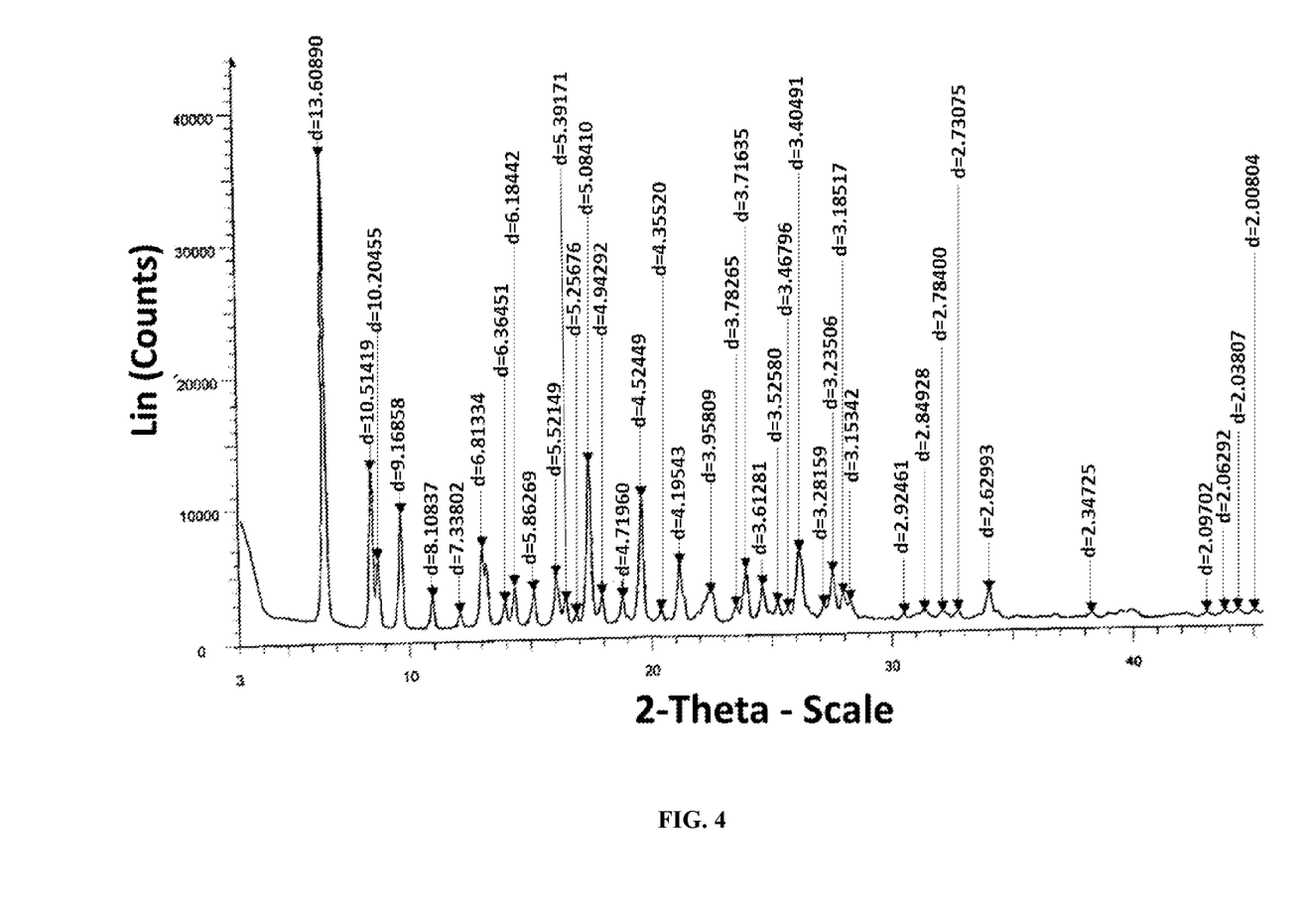
FIG. 4: Illustrates the PXRD pattern of crystalline Form B of (5)-N-(1-Carboxy-2-Methyl-Prop-1-yl)-N-Pentanoyl-N-[2'-(1H-Tetrazol-5-yl)-Biphenyl-4-yl-Methyl]-Amine disodium salt.

The PXRD pattern of Form B of (S)—N-(1-Carboxy-2-Methyl-Prop-1-yl)-N-Pentanoyl-N-[2'-(1H-Tetrazol-5-yl)-Biphenyl-4-yl-Methyl]-Amine disodium salt is shown in FIG. 4.

IR (cm$^{-1}$): 561.00, 669.42, 746.37, 760.47, 785.74, 814.68, 861.08, 942.02, 974.87, 1011.05, 1101.83, 1137.16, 1176.23, 1203.48, 1265.48, 1303.84, 1359.14, 1405.62, 1459.74, 1507.88, 1618.07, 2871.76, 2931.82, 2960.36, 3406.61.

Figure 5:
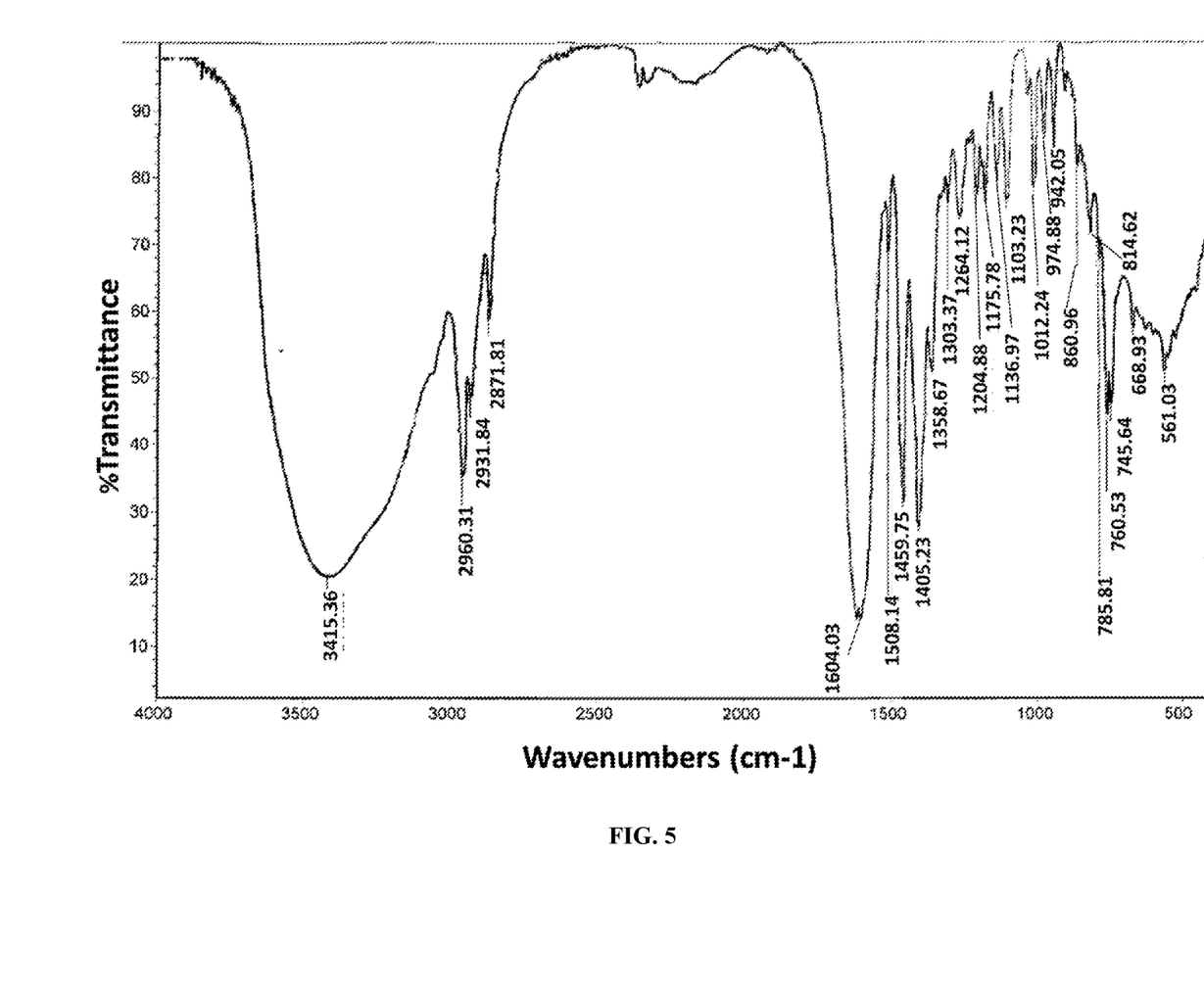
FIG. 5: Illustrates the IR pattern of crystalline Form B of (S)—N-(1-Carboxy-2-Methyl-Prop-1-yl)-N-Pentanoyl-N-[2'-(1H-Tetrazol-5-yl)-Biphenyl-4-yl-Methyl]-Amine disodium salt.

The IR pattern of crystalline Form B of (S)—N-(1-Carboxy-2-Methyl-Prop-1-yl)-N-Pentanoyl-N-[2'-(1H-Tetrazol-5-yl)-Biphenyl-4-yl-Methyl]-Amine disodium salt is shown in FIG. 5.

Example 8: Preparation of Crystalline Form P of (S)—N-(1-Carboxy-2-Methyl-Prop-1-yl)-N-Pentanoyl-N-[2'-(1H-Tetrazol-5-yl)-Biphenyl-4-yl-Methyl]-Amine Disodium Salt To a solution of amorphous (S)—N-(1-Carboxy-2-Methyl-Prop-1-yl)-N-Pentanoyl-N-[Z-(1H-Tetrazol-5-yl)-Biphenyl-4-yl-Methyl]-Amine (2.0 g) in 100 ml toluene was added 50% aq. sodium hydroxide (0.38 g.) solution. The temperature of reaction mass was raised to reflux and water was removed azeotropically. During azeotropic distillation, clear solution gradually transformed to crystalline suspension. The suspension was cooled to 85-90° C. The suspension mass was stirred at same temperature for 15-30 min. Filtered the reaction mass. The wet cake was dried for 10-12 hr at 30-35° C. under vacuum to yield crystalline Form P of (S)—N-(1-Carboxy-2-Methyl-Prop-1-yl)-N-Pentanoyl-N-[2'-(1H-Tetrazol-5-yl)-Biphenyl-4-yl-Methyl]-Amine disodium salt (1.81 g).

Figure 6:
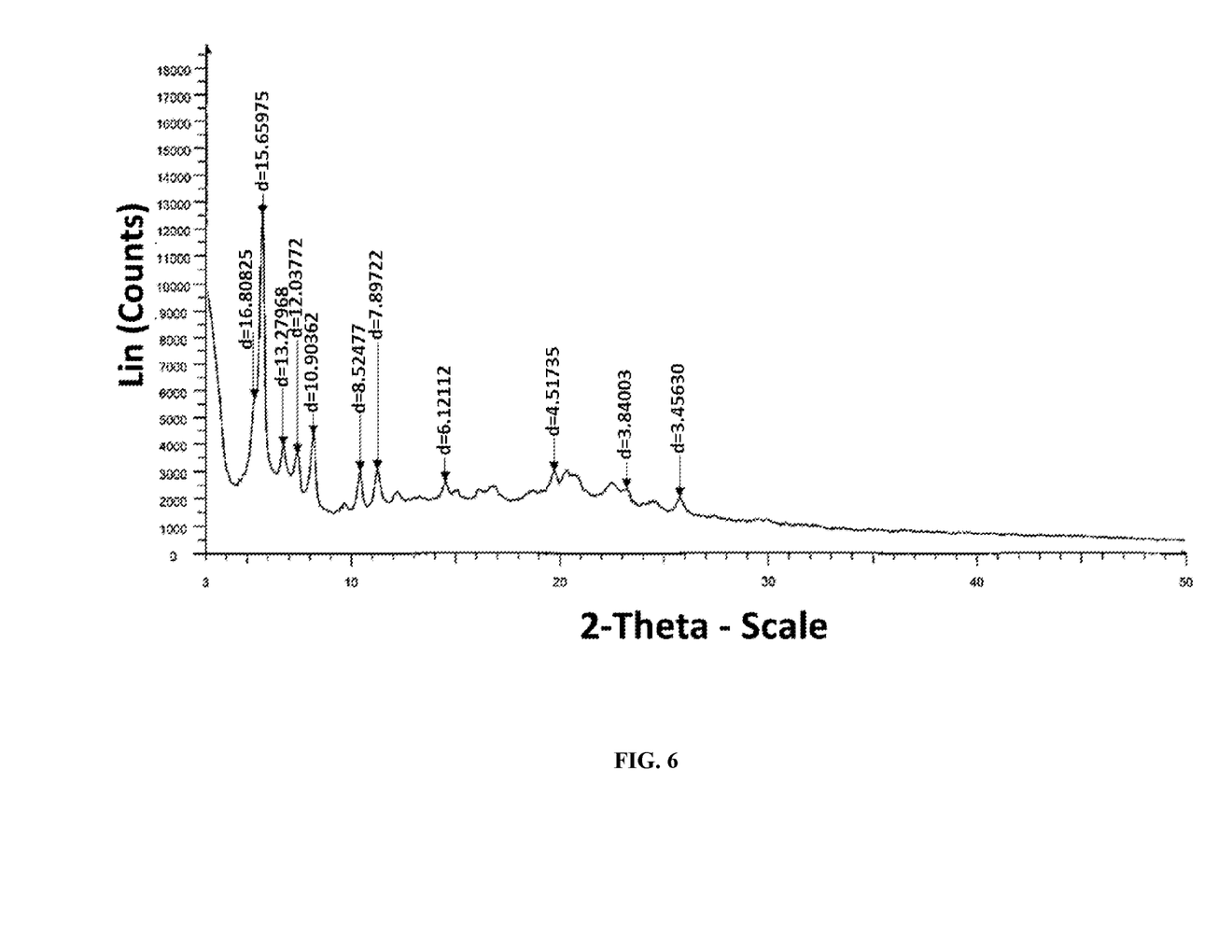
FIG. 6: Illustrates the PXRD of crystalline Form P of (S)—N-(1-Carboxy-2-Methyl-Prop-1-yl)-N-Pentanoyl-N-[2'-(1H-Tetrazol-5-yl)-Biphenyl-4-yl-Methyl]-Amine disodium salt.

The PXRD pattern of Form P of (S)—N-(1-Carboxy-2-Methyl-Prop-1-yl)-N-Pentanoyl-N-[2'-(1H-Tetrazol-5-yl)-Biphenyl-4-yl-Methyl]-Amine disodium salt is shown in FIG. 6.

IR (cm$^{-1}$): 561.01, 744.43, 760.41, 941.64, 975.11, 1013.32, 1105.33, 1135.85, 1175.04, 1207.25, 1262.49, 1361.28, 1404.28, 1459.85, 1507.61, 1629.05, 2871.74, 2959.93, 3420.93.

Example 9: Preparation of Amorphous Form of Sacubitril Valsartan Trisodium

Trisodium Sacubitril valsartan (1.0 g.) was dissolved in a mixture of Heptane (50 ml) and Ethylene glycol (0.22 g.) mixture under reflux temperature. Removal of water from the reaction mass was done by azeotropic distillation followed by stripping off five times with fresh Heptane. The suspension was cooled to 25-30° C. The suspension mass was stirred at same temperature for 15-30 min. Filtered the reaction mass. The wet cake was dried for 10-12 hr at 30-35° C. under vacuum to yield Amorphous Form of Sacubitril valsartan trisodium. Moisture Content 2.38%.

Example 10: Preparation of Amorphous Form of Sacubitril Valsartan Trisodium

Trisodium Sacubitril valsartan (1.0 g.) was dissolved in a mixture of Heptane (50 ml) and Ethylene glycol (0.11 g.) mixture under reflux temperature. Removal of water from the reaction mass was done by azeotropic distillation followed by stripping off five times with fresh Heptane. The suspension was cooled to 25-30° C. The suspension mass was stirred at same temperature for 15-30 min. Filtered the reaction mass. The wet cake was dried for 10-12 hr at 30-35° C. under vacuum to yield Amorphous Form of Sacubitril valsartan trisodium. Moisture Content 1.35%.

Example 11: Preparation of Amorphous Form of Sacubitril Valsartan Trisodium

Trisodium Sacubitril valsartan (1.0 g.) was dissolved in a mixture of Heptane (50 ml) and Propane 1,2 diol (0.27 g.) mixture under reflux temperature. Removal of water from the reaction mass was done by azeotropic distillation followed by stripping off five times with fresh Heptane. The suspension was cooled to 25-30° C. The suspension mass was stirred at same temperature for 15-30 min. Filtered the reaction mass. The wet cake was dried for 10-12 hr at 30-35° C. under vacuum to yield Amorphous Form of Sacubitril valsartan trisodium. Moisture Content 2.48%.

Example 12: Preparation of Amorphous Form of Sacubitril Valsartan Trisodium

Trisodium Sacubitril valsartan (1.0 g.) was dissolved in a mixture of Heptane (50 ml) and Propane 1,2 diol (0.13 g.)

mixture under reflux temperature. Removal of water from the reaction mass was done by azeotropic distillation followed by stripping off five times with fresh Heptane. The suspension was cooled to 25-30° C. The suspension mass was stirred at same temperature for 15-30 min. Filtered the reaction mass. The wet cake was dried for 10-12 hr at 30-35° C. under vacuum to yield Amorphous Form of Sacubitril valsartan trisodium. Moisture Content 2.46%.

Example 13: Preparation of Amorphous Form of Sacubitril Valsartan Trisodium

Trisodium Sacubitril valsartan (1.0 g.) was dissolved in a mixture of Heptane (50 ml) and Butane 2,3 diol (0.32 g.) mixture under reflux temperature. Removal of water from the reaction mass was done by azeotropic distillation followed by stripping off five times with fresh Heptane. The suspension was cooled to 25-30° C. The suspension mass was stirred at same temperature for 15-30 min. Filtered the reaction mass. The wet cake was dried for 10-12 hr at 30-35° C. under vacuum to yield Amorphous Form of Sacubitril valsartan trisodium. Moisture Content 2.2%.

Example 14: Preparation of Amorphous Form of Sacubitril Valsartan Trisodium

Trisodium Sacubitril valsartan (1.0 g.) was dissolved in a mixture of Heptane (50 ml) and Butane 2,3 diol (0.16 g.) mixture under reflux temperature. Removal of water from the reaction mass was done by azeotropic distillation followed by stripping off five times with fresh Heptane. The suspension was cooled to 25-30° C. The suspension mass was stirred at same temperature for 15-30 min. Filtered the reaction mass. The wet cake was dried for 10-12 hr at 30-35° C. under vacuum to yield Amorphous Form of Sacubitril valsartan trisodium. Moisture Content 1.8%.

Example 15: Preparation of Amorphous Form of Sacubitril Valsartan Trisodium

To a solution of Sacubitril calcium (1.0 Kg) in ethyl acetate (7.0 L) added 2N HCl to neutralize at 15-20èC. Organic layer was washed with dil. HCl followed by water and brine solution. The organic layer was added with Valsartan (0.97 Kg), ethyl acetate and aq. Sodium hydroxide solution (0.64 Kg). Distilled off the ethyl acetate and reaction mass was stripped of with ethyl acetate thrice (2 L×3). The reaction mass was added with ethyl acetate (5 L), heptane (25 L) and propanediol (0.053 Kg) to the reaction mass at 25-30èC. The reaction mass was heated to reflux. The solvent in the reaction mass was partially (15.0 Vol.) distilled off and reaction mass was stripped off with heptane thrice. Maintain the reaction mass at reflux temperature for an hour. Cool the reaction mass to 25-30èC. Filtered off the product and washed the wet cake with heptane. The product was dried at 60èC to yield (1.69 Kg) of Amorphous Form of Sacubitril valsartan trisodium.

Figure 7:
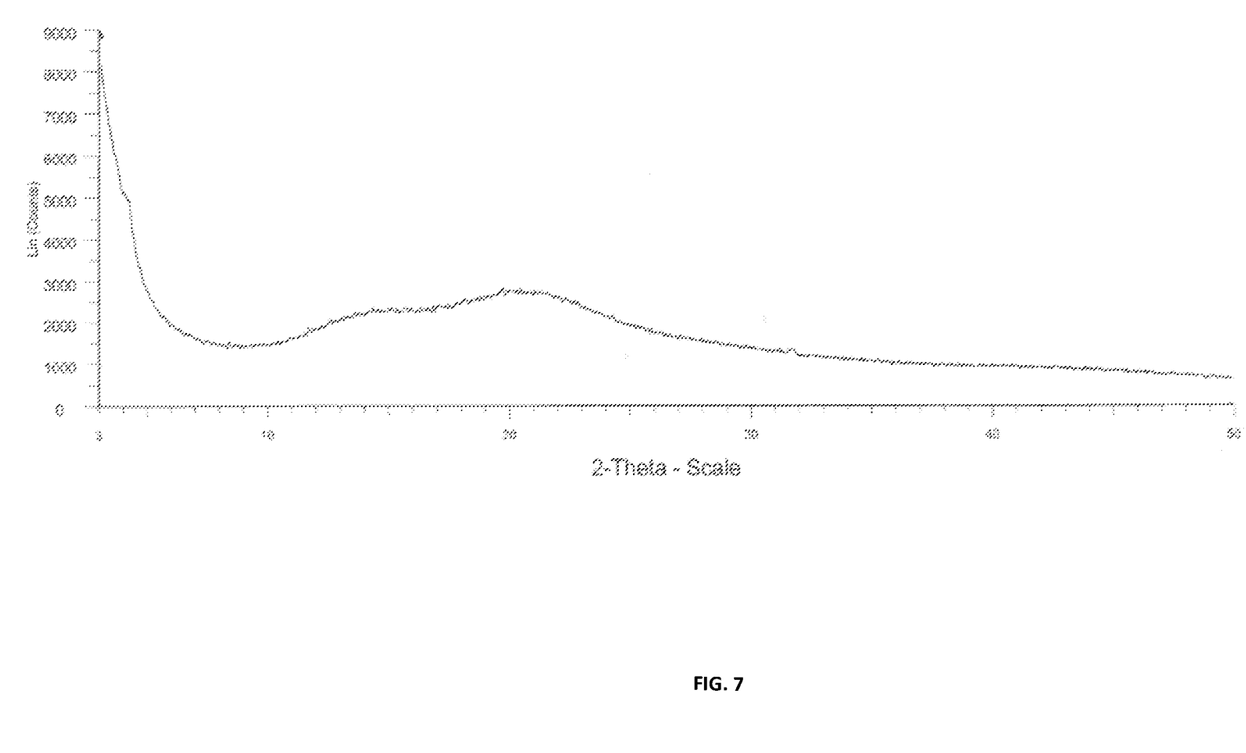
FIG. 7: Illustrates the PXRD pattern of amorphous form of Sacubitril valsartan trisodium complex.

The PXRD pattern of amorphous form of Sacubitril valsartan trisodium complex is shown in FIG. 7.

Example 16: Preparation of Amorphous Solid Dispersion of Trisodium Sacubitril Valsartan With Silicified Micro Crystalline Cellulose To a solution of Sacubitril calcium in ethyl acetate (7.0 vol) added 2N HCl (2.5 vol) to neutralize at 15-20 èC. Organic layer was washed with dil. HCl followed by water and brine solution. The organic layer was added with Valsartan, ethyl acetate (13 vol) and aq. Sodium hydroxide solution (3.0 eq) followed by silicified micro crystalline cellulose (100% w/w) to the reaction mass. Distil off the ethyl acetate and strip of with ethyl acetate trice in order to control the moisture. Add ethyl acetate (5 vol), heptane (25 vol) and propanediol (0.3 eq) to the reaction mass at 25-30 èC. Heat the reaction mass to the reflux. Remove the solvent (15 vol) and add same amount of heptane trice in order to get rid of ethyl acetate and moisture. Maintain the reaction mass at reflux temperature for an hour. Cool the reaction mass to 25-30èC. Filter the product under nitrogen atmosphere and wash the wet cake with heptane. Dry the product at 60èC.

Example 17: Preparation of Amorphous Solid Dispersion of Trisodium Sacubitril Valsartan With Mannitol To a solution of Sacubitril calcium in ethyl acetate (7 vol) added 2N HCl (2.5 vol) to neutralize at 15-20 èC. Organic layer was washed with dil. HCl followed by water and brine solution. The organic layer was added with Valsartan, ethyl acetate (13 vol) and aq. Sodium hydroxide solution (3.0 eq) followed by mannitol (100% w/w) to the reaction mass. Distil off the ethyl acetate and strip of with ethyl acetate trice in order to control the moisture. Add ethyl acetate (5 vol), heptane (25 vol) and propanediol (0.3 eq) to the reaction mass at 25-30èC. Heat the reaction mass to the reflux. Remove the solvent (15 vol) and add same amount of heptane trice in order to get rid of ethyl acetate and moisture. Maintain the reaction mass at reflux temperature for an hour. Cool the reaction mass to 25-30èC. Filter the product under nitrogen atmosphere and wash the wet cake with heptane. Dry the product at 60èC.

The invention claimed is:

1. A process for the preparation of crystalline form B of sacubitril sodium, the process comprising:
   a) treating sacubitril with a sodium source to form a reaction mixture;
   b) heating the reaction mixture and azeotropic removal of water from the reaction mixture; and
   c) isolating the crystalline form B of sacubitril sodium; and wherein the crystalline form sacubitril sodium has a PXRD pattern as shown in FIG. 3.

2. The process according to claim 1, wherein the sodium source is selected from the group consisting of sodium hydroxide, sodium carbonate, sodium bicarbonate, sodium methoxide, and sodium ethoxide.

* * * * *